(12) United States Patent
Bauer

(10) Patent No.: US 8,548,588 B1
(45) Date of Patent: Oct. 1, 2013

(54) CRM-DEVICE VENTRICULAR-PACING BLANKING CONTROL

(71) Applicant: Peter T. Bauer, Portland, OR (US)

(72) Inventor: Peter T. Bauer, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 0 days.

(21) Appl. No.: 13/624,679

(22) Filed: Sep. 21, 2012

(51) Int. Cl.
*A61N 1/00* (2006.01)

(52) U.S. Cl.
USPC .................................................. 607/18

(58) Field of Classification Search
USPC ................ 607/18, 4, 5, 17, 27; 600/513
See application file for complete search history.

(56) References Cited

U.S. PATENT DOCUMENTS

| | | | |
|---|---|---|---|
| 5,392,780 A | 2/1995 | Ogino et al. | |
| 5,758,654 A | 6/1998 | Burton-Krahn et al. | |
| 6,979,297 B2 | 12/2005 | Andresen et al. | |
| 7,039,538 B2 | 5/2006 | Baker, Jr. | |
| 7,072,708 B1 | 7/2006 | Andresen et al. | |
| 7,074,195 B2 | 7/2006 | Nelson et al. | |
| 7,096,060 B2 | 8/2006 | Arand et al. | |
| 7,113,820 B2 | 9/2006 | Schlegel et al. | |
| 7,171,269 B1 | 1/2007 | Addison et al. | |
| 7,174,203 B2 | 2/2007 | Arand et al. | |
| 7,225,021 B1 | 5/2007 | Park et al. | |
| 7,248,923 B2 * | 7/2007 | Maile et al. ............. 607/17 |
| 7,302,290 B2 | 11/2007 | Bauer | |
| 7,424,321 B2 | 9/2008 | Wariar et al. | |
| 7,435,221 B1 | 10/2008 | Bharmi et al. | |
| 7,437,699 B2 | 10/2008 | Morita et al. | |
| 7,559,903 B2 | 7/2009 | Moussavi et al. | |
| 7,668,589 B2 | 2/2010 | Bauer | |
| 7,819,814 B2 | 10/2010 | Gavriely et al. | |
| 8,065,002 B2 | 11/2011 | Arand et al. | |
| 8,105,241 B2 | 1/2012 | Nelson et al. | |
| 8,137,283 B2 | 3/2012 | Syeda-Mahmood et al. | |
| 2002/0188329 A1 | 12/2002 | Struble | |
| 2003/0187337 A1 | 10/2003 | Tarassenko et al. | |
| 2004/0127792 A1 | 7/2004 | Siejko et al. | |
| 2004/0230105 A1 | 11/2004 | Geva et al. | |
| 2005/0027323 A1 | 2/2005 | Mulligan et al. | |
| 2005/0080348 A1 | 4/2005 | Stahmann et al. | |
| 2005/0222515 A1 | 10/2005 | Polyshchuk et al. | |
| 2006/0079942 A1 * | 4/2006 | Deno et al. ............. 607/17 |
| 2006/0155202 A1 | 7/2006 | Arand et al. | |
| 2007/0038137 A1 | 2/2007 | Arand et al. | |
| 2007/0055151 A1 | 3/2007 | Shertukde et al. | |
| 2007/0191725 A1 | 8/2007 | Nelson | |

(Continued)

FOREIGN PATENT DOCUMENTS

CA 1256507 6/1989

Primary Examiner — Robert N Wieland

(74) Attorney, Agent, or Firm — Jon M. Dickinson, P.C.

(57) ABSTRACT

A system, operatively connectable both to a cardiac-rhythm-management (CRM) subject, and to a CRM device associated with that subject, and an associated method, operable, in relation to received-and-processed, real-time, CRM-subject-specific, simultaneous ECG and heart-sound information, and other information including measurement time markers where available, for blocking, under all circumstances during the ventricular relative refractory period lying within each of successive CRM-subject cardiac cycles occupying a span of such cycles, the ventricular pacing activity of the subject-associated CRM device—the beginning and ending of such blocking in each cardiac cycle being system-defined to lie preferably, and respectively, (a) within the real-time, ventricular depolarization window in the cycle, and (b) at the time of the real-time, S2 heart-sound, plus or minus any user-defined time-delta.

15 Claims, 2 Drawing Sheets

(56) References Cited

U.S. PATENT DOCUMENTS

Figure 1:
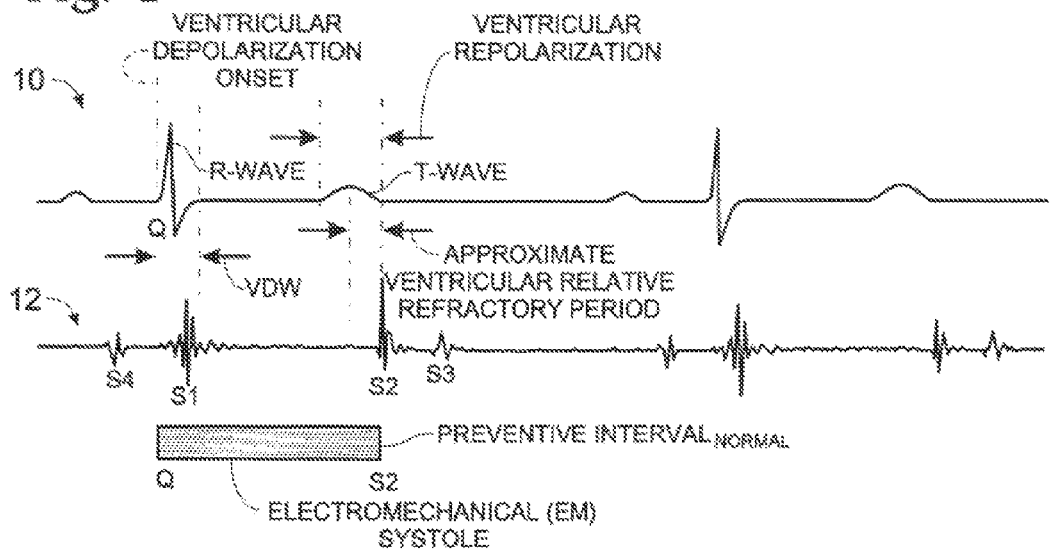

| | | |
|---|---|---|
| 2008/0021510 A1 | 1/2008 | Mi et al. |
| 2008/0125820 A1* | 5/2008 | Stahmann et al. ............... 607/4 |
| 2008/0177191 A1 | 7/2008 | Patangay et al. |
| 2008/0255465 A1 | 10/2008 | Nelson |
| 2009/0112107 A1 | 4/2009 | Nelson et al. |
| 2009/0112108 A1 | 4/2009 | Nelson et al. |
| 2009/0165559 A1 | 7/2009 | Lec |
| 2010/0094148 A1 | 4/2010 | Bauer et al. |
| 2010/0331903 A1* | 12/2010 | Zhang et al. ..................... 607/5 |
| 2012/0296228 A1* | 11/2012 | Zhang et al. ................. 600/513 |
| 2013/0030484 A1* | 1/2013 | Zhang et al. ................... 607/17 |

* cited by examiner

CRM-DEVICE VENTRICULAR-PACING BLANKING CONTROL

BACKGROUND AND SUMMARY OF THE INVENTION

This invention relates to cardiac rhythm management, and in particular to the implementation of systemic and methodologic time-interval (preventive-interval) blanking (or blocking) control over the ventricular pacing activity of cardiac-rhythm-management (CRM) devices.

There are many people, referred to herein as CRM subjects, or simply as subjects, who are challenged by certain compromising heart conditions that result in their being equipped, either internally (by implantation) or externally, with a cardiac-rhythm-management (CRM) device, such as a pacemaker.

CRM devices—pacemakers being good illustrations—have a commendable history of safely and confidently controlling, when necessary by the action of applying to the heart properly timed, machine-implemented (i.e., non-intrinsic), cardio-ventricular pacing pulses, cardiac-cycle rhythm in CRM subjects whose compromised heart behavior, in relation to intrinsic ventricular pacing, may be erratic, or in other ways undependable. Such devices are typically designed and programmed to apply a properly timed, non-intrinsic (what is also referred to herein as an electro-artificial) ventricular pacing pulse whenever they detect the absence in a CRM subject of a properly timed, intrinsic, ventricular pacing pulse—the important electrical pulse which functions to initiate ventricular depolarization, and which marks the beginning of the electromechanical (EM) systole in a subject's cardiac cycle. The end of the EM systole is marked by the S2 heart sound.

Generally speaking, all is normally remarkably, and comfortably, well in this realm of electro-artificial (non-intrinsic), cardio-functionality assistance until something, for some reason, causes a CRM device to deliver a non-intrinsic ventricular pacing pulse, referred to herein as an errant pulse, at the wrong time in a CRM subject's cardiac cycle, such as at the wrong moment (potentially dangerously) within, and beyond the beginning of, the electromechanical (EM) systole in the cycle, and in particular, during that part of the EM systole which contains the critical latter portion of the T-wave which portion includes what is known as the ventricular relative refractory period. An inadvertent (errant), non-intrinsic, ventricular pacing pulse delivered during this critical period—a time when ventricular cells are subject to activation—is extraordinarily dangerous.

Such an errant, non-intrinsic pulse can initiate either one of the dangerous, and often quickly fatal, heart behaviors known as ventricular fibrillation and pacemaker-mediated tachycardia, and this possibility obviously must be avoided.

The present invention—a safety-enhancing invention—relates specifically to such CRM subjects, and to the associated world of CRM ventricular pacing, and features a method and a system, based in part upon the use of heart-sound information along with other information, for preventing the potentially fatal consequence of such a device's pacing timing accidentally triggering ventricular fibrillation or pacemaker-mediated tachycardia by dangerously applying to the heart a wrongly timed, non-intrinsic ventricular pacing pulse, such as by delivering a pacing pulse during a confounding condition which may so deteriorate ECG signal information that proper timing operation of the device becomes compromised. The invention, which is computer-based, and which operates with suitable, conventionally established, algorithmic programming, accomplishes this prevention through imposing on a CRM device an appropriately time-interval-defined and established CRM control signal which, throughout the control duration time of this defined interval—referred to herein variously as a preventive interval, as a blanking interval, as a time interval determined, at least in part, in timed relation to a CRM subject's S2 heart sound, as a blanking-time duration, as a blanking interval, and as a blanking-time control duration—positively inhibits CRM ventricular-pacing activity.

While a potentially successful, imposed blanking (preventive) interval could have different, selected, overall lengths and beginning times in a cardiac cycle (as discussed hereinbelow), as long as all such intervals have lengths and time positions that fully bracket the entirety in the cycle of the ventricular relative refractory period, the preferred, and most conservatively safe practice of the present invention establishes a preventive interval that begins at ventricular depolarization onset (the beginning of the EM systole), and ends at a time which either (a) is coincident with the time of the S2 heart sound in each cardiac cycle, or (b) is at a time based upon the time of the S2 heart sound, plus or minus an optional, user determined time delta—a time addition or subtraction registered (perhaps initially and/or periodically as desired) in the computer-based system of the invention. Such a time delta, if any is deemed to be useful, is one which may be selected at any time by a medical professional who looks at an appropriate collection of subject-specific ECG waveform cycle data to decide where the associated T-wave seems regularly to exist in the subject's cardiac cycles. A T-wave which ends, for example, regularly after the associated S2 heart sound will dictate the preferred use of an appropriate "plus" time delta, whereas a T-wave which ends regularly before the associated S2 heart sound may justify the use of a "minus" time delta. The purpose of time-delta usage is to set the end of a preventive interval to occur soon after the end of the T-wave.

Regarding the time for beginning a preventive blanking interval, in accordance with practice of the present invention, other than at the most safe, and most conservative, time of ventricular depolarization onset, as just mentioned, all will be comfortably safe so long as this interval begins at any time before the ventricular relative refractory period. For examples, very good, other starting times all fall (at least some as well-recognized ECG and heart-sound fiducial markers) within the ventricular depolarization window (from and including the time of its beginning to the time of its ending), and include, representationally, the time of the peak of the R-wave, the time of the S1 heart sound, the time of the conclusion of the ventricular depolarization window, as well, optionally additionally, as selected times of specifically made, within-ventricular-depolarization-window measurements, such as measurements of intracardiac and/or intrathoracic impedance, intracardiac and/or intrathoracic pressure, blood pressure, oxygen saturation, and pulse—referred to collectively herein as other-source measurement time markers, or information. These measurement time markers and information, where made available, may so be made available for use by the system of the invention readily, and conventionally, during the ventricular depolarization window in each cardiac cycle. For example such markers and information may be made available, each where desired, as an input to signal-processing structure in the system of the invention by a CRM device to which the system is operatively connected, and which has been "instructed" to furnish such information, in each cardiac cycle, derived from conventionally provided-to-it, related input information.

Accordingly, the present invention, from a structural point of view, generally features a computer-based system for blocking, under all circumstances during the ventricular relative refractory period in each of a CRM subject's cardiac cycles, the ventricular pacing activity of an associated CRM device—the beginning and ending of such blocking in each cardiac cycle being system-defined to lie, respectively, (a) within the real-time, ventricular depolarization window in the cycle, and (b) at the time of the real-time, S2 heart-sound, plus or minus any user-defined time-delta.

In different ways, and according to user wishes, the system of the invention, which includes operatively interconnected signal-processing and control-signal-generating structures, may be wholly, or partially, integrated with a CRM subject's CRM device internal or external.

More specific structural features will be discussed below in the detailed description of the invention.

From a general methodological point of view, the invention features a signal-processing method employable in preparation for per-cardiac-cycle blanking of the ventricular pacing operation of a CRM subject's associated CRM device during a blanking time interval within each of the CRM subject's cardiac cycles, which interval always includes the ventricular relative refractory period in the cycle, this method including the steps of generating, and then making available for potential application to the CRM subject's associated CRM device, a ventricular-pacing blanking-time CRM control signal which, through appropriate method-implemented signal processing of (a) received, real-time, CRM-subject-specific, simultaneous ECG and heart-sound information, and of (b) optionally received other information including measurement time markers, has been established with a duration relating to the spaced timings of cardiac-cycle-specific ventricular depolarization and subsequent S2 heart-sound information.

Further specifics of the invention methodology are presented below herein.

These and various other features and advantages of and offered by the system and methodology of the present invention will become more fully apparent as the detailed description of it which follows is read in conjunction with the accompanying drawings.

DESCRIPTIONS OF THE DRAWINGS

FIG. 1 presents, on a common time scale, but in a manner which is not internally drawn to scale, an illustration of real-time, simultaneous ECG electrical and heart-sound waveforms received, via appropriate sensors, from a CRM subject during a pair of successive, substantially normal cardiac cycles. Labeled in this figure, in relation to one of the pictured cycles, are several important ECG and heart-sound markers and periods of cardiac activity, including intrinsic-Q-wave-initiated Ventricular Depolarization Onset, the Ventricular Depolarization Window (marked VDW), the R-Wave, the S1 and S2 heart sounds, the Electromechanical (EM) Systole (Q-S2—represented by a shaded bar-graph, the electrical T-Wave which, in time, correspondingly defines the labeled period of Ventricular Repolarization, and the Approximate Ventricular Relative Refractory Period which resides within the latter portion of the T-wave.

In this figure, the T-wave is shown in a relatively normal condition ending, essentially, on, or just immediately before, the occurrence of the S2 heart sound. With the T-wave disposed in the "normal" time position shown for it in FIG. 1, the Q-S2 time interval, represented by the shaded bar graph, constitutes what is referred to herein as a normal preventive interval, which interval represents the most preferable, and the safest interval for implementing ventricular pacing blocking. For this reason, the bar-graph is also labeled Preventive Interval$_{Normal}$.

Figure 2:
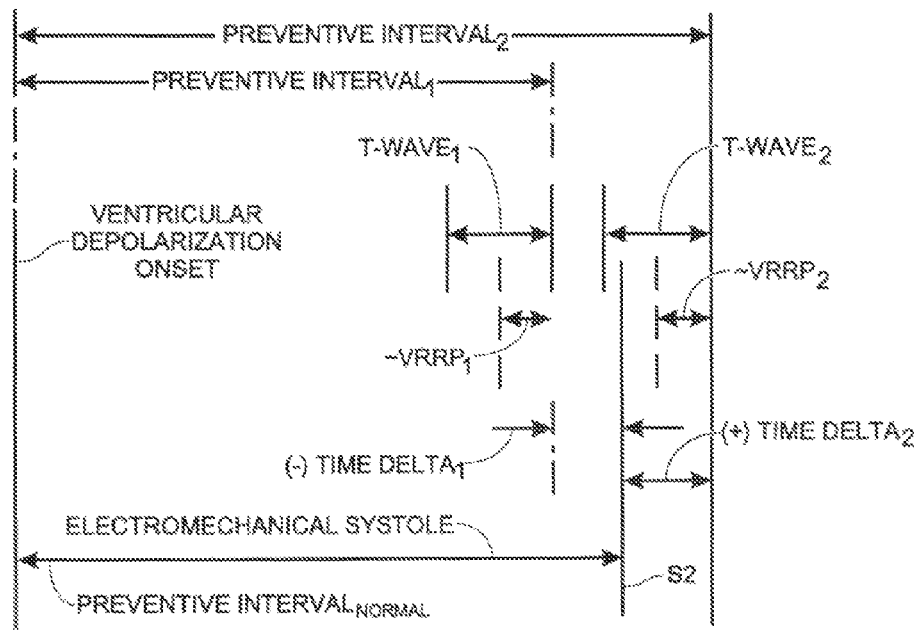

FIG. 2, which has a clear, cardiac-cycle-informational marker and time-period relationship to FIG. 1, though it is quite different from FIG. 1, is a schematic, time-based, vertical marker-line illustration showing certain, relative, time-positional locations, and associated, time-period durations, representing, in a purposely exaggerated manner, two, different, representative, non-normal CRM-subject heart conditions that involve two, different, non-normal cardiac-cycle positions of a T-wave. One of these positions has the T-wave ending noticeably ahead of the S2 heart sound by a labeled (−)Time Delta$_1$, and the other has the T-wave in a position bracketing the S2 heart sound, and ending noticeably thereafter by a labeled (+)Time Delta$_2$.

FIG. 2 further includes labeling identifying three different, representative preventive or pacing-blanking intervals, including, in addition to the "normal" preventive interval shown in FIG. 1 (the associated, "normal-position" T-wave, seen in FIG. 1, is omitted from FIG. 2), Preventive Interval$_1$ and Preventive Interval$_2$, which latter, two intervals relate specifically to the pictured, two, different, non-normal T-Wave$_1$ and T-Wave$_2$ time locations, and to the pictured, two, different, schematically represented, ventricular relative refractory periods VRRP$_1$ and VRRP$_2$ that are associated, respectively, with these same, two, different, non-normal T-wave time locations.

Matters shown in FIG. 2 are also not drawn to scale.

As will become apparent, many of the manners of operation of the system of the present invention, insofar as timings are concerned, are effectively fully illustrated in and by these two drawing figures.

Figure 3:
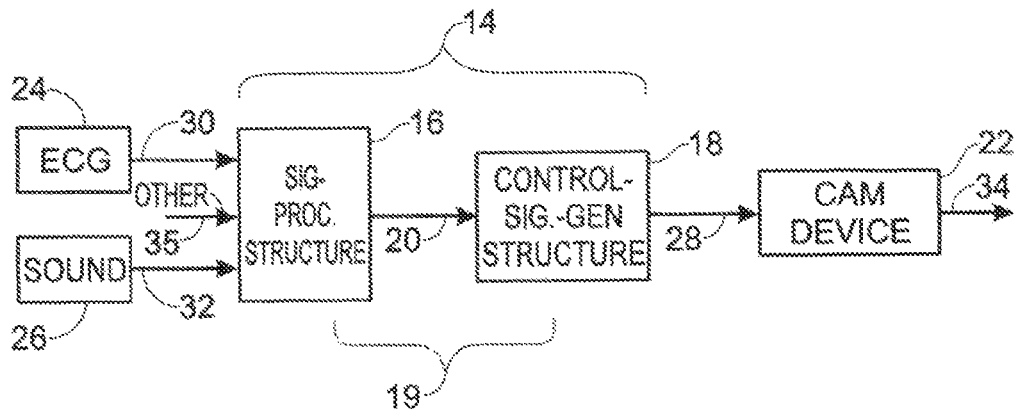

FIG. 3 is a simplified, block/schematic diagram illustrating, in operative conditions relative to a CRM device, to ECG and sound sensors, and to an optional "Other" input structure which has an optional operative connection (not specifically fully illustrated) to a CRM device, one preferred form—an external form—of the system of the present invention. This figure additionally functions, as will be explained below, to picture several, different, proposed system modifications (anatomy-external and anatomy-internal). A small, horizontal bracket drawn at the base of this figure represents conventionally algorithmically programmed computer structure which is distributively included in the two system blocks appearing immediately above it.

Figure 4:
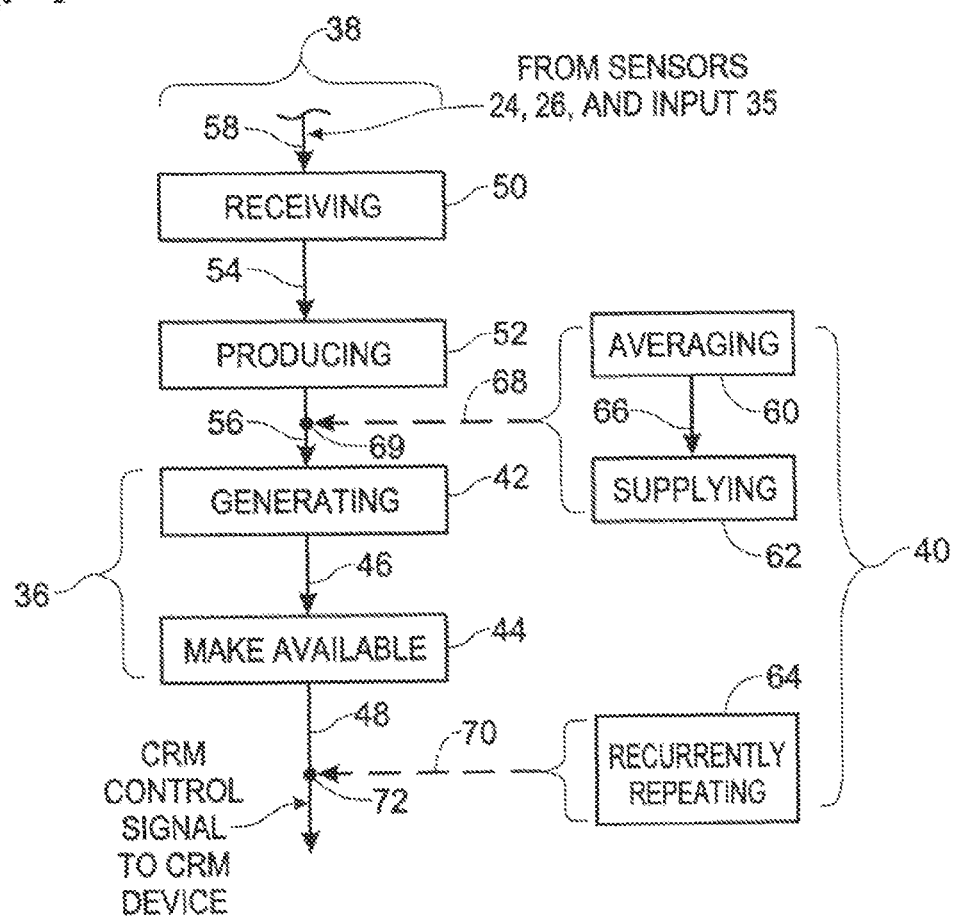

FIG. 4 is a simplified, block/schematic diagram which is employed herein to illustrate different modalities for practicing the methodology of the present invention.

DETAILED DESCRIPTION OF THE INVENTION

Turning now to the drawings, and referring first of all to FIGS. 1 and 2, indicated generally in FIG. 1 at 10 and 12, respectively, are ECG and heart-sound waveforms acquired simultaneously from a CRM subject (not shown). These waveforms picture, essentially, two, complete, successive cardiac cycles of that subject. For the purpose of initial discussion herein respecting these two waveforms, we will assume that they have been collected through appropriately anatomically attached, external sensors that are disposed on the outside of the subject's anatomy.

As was mentioned above in relation to the description of FIG. 1, the cardiac cycles which are pictured in this figure are substantially normal, each being triggered, to produce ventricular onset in the cycle, by an intrinsic Q-wave, with the T-wave in each cycle (not drawn to any, particular configurational scale) disposed in a manner whereby it ends substantially simultaneously, or perhaps slightly before, the S2 heart sound in the cycle.

Regarding the triggering of ventricular depolarization in a cardiac cycle, it is well understood that, with respect to a CRM subject, it is possible that such triggering might be effected, rather than by an intrinsic Q-wave, by a non-intrinsic ventricular pacing pulse applied to the subject's heart by the subject's associated CRM device, such as by an implanted pacemaker.

Inasmuch as the successful performance of the methodology of the present invention depends upon accurate, per-cycle determinations of the timings of both ventricular depolarization onset and the S2 heart sound, where the beginning of a cardiac cycle is marked, as is possible, by two, closely time-spaced, apparent ventricular pacing pulses, one of which is intrinsic, and the other non-intrinsic, it is important that the system of the invention be able to determine/identify, by a process of practical selection, which of these two, "time-competing" pulses is actually to be "treated" as being responsible for ventricular-depolarization onset. A resolution determination respecting this question, which is not specifically a part of the present invention, may be performed in a number of ways well known to those skilled in the art.

Identifications of the peak of the R-wave, and of the span and end point of the ventricular depolarization window, follow easily from identification of ventricular depolarization onset.

Acoustic detections of the useful S1 heart sound, and of the especially important S2 heart sound, in relation to practice of the invention, are usually relatively simple matters that do not normally create any timing-identification complications. There are many known, conventional ways of acquiring this information successfully—not part of the present invention.

FIG. 1 is appropriately labeled to indicate the presences of these several, useful fiducials and markers in the ECG and heart sound waveform information.

From what has been described so far, and introducing here repeated emphasis, it should be clear that, under all cardiac-cycle circumstances, as long as a subject's CRM device is confirmedly prevented from applying to the heart a ventricular pacing pulse during a time when the ventricular cells could be activated, the possibility of an errantly-delivered, CRM-device ventricular pacing pulse causing either one of the dangerous, and potentially fatal, heart conditions identified above will be confidently eliminated. To assure such confident possibility-elimination, the system and methodology of the invention are structured to create a "widely-visioned" margin of safety based upon the establishment, for blanking-control use, of a preventive, pacing-blanking interval which, while launchable user-selectively in a cardiac cycle at potentially several different times mentioned below, and ending always in close timed relationship to the time of the S2 heart sound (as will further be explained), in all cases comfortably covers the critical ventricular relative refractory period in a cycle. Selectively different starting points for the initiating of pacing-blanking control, as proposed herein, all create safely preventive, but selectively different, pacing-blanking intervals having closely related, but specifically different, overall lengths.

Preferably, and most safely, the beginning of a preventive interval in a cardiac cycle according to practice of the invention, occurs at the time of onset of ventricular depolarization—a beginning easily accomplished through readily detecting and then using, the very obvious time of the cycle-launching Q-wave or non-intrinsic CRM ventricular pacing pulse, as presented unambiguously by electrical, ECG waveform data. Other quite safely usable starting times, all necessarily existing, or otherwise set, within the ventricular depolarization window, include the time of the peak of the R-wave, the time of the S1 heart sound, the time of the ending of the ventricular depolarization window, and optionally additionally, the times (user selectable) of certain readily conventionally made (usually on a per-cycle basis within the ventricular depolarization window), and furnished, measurements, such as measurements of intracardiac and/or intrathoracic impedance, intracardiac and/or intrathoracic pressure, blood pressure, oxygen saturation, and pulse—referred to collectively herein as other-source measurement time markers, or information. Such measurements may be made by appropriate, conventional sensors, conductive connections, etc., and supplied to a subject's CRM device through conventional data input structure normally provided in such a device, for furnishing by that device, as per-cycle, within ventricular-depolarization-window output information, to the system of the present invention.

According to the present invention, ending the preventive interval confirmedly following completion of the ventricular relative refractory period is also easily accomplished by using, for this purpose, and in the context of employing any optionally selected user-predetermined plus or minus time delta, the unambiguous acoustic presence of the cycle's mechanically associated S2 heart sound, the time location of which sound in a cardiac cycle is presented very readably as a definitive time marker in acquired sound-data waveform information. Use of the S2 heart-sound time marker for establishing preventive-interval ending, a special feature of the present invention, avoids placing per-cycle risky, end-of preventive-interval reliance on determining exact T-wave time location from electrical ECG data—an avoidance which is important, inasmuch as there often exists appreciable ambiguity surrounding clear identification of T-wave time location in acquired electrical data.

A preventive interval so established will always reliably cover a cycle time span which will "capture" protectively all possible periods of ventricular cell vulnerability to pacing activation. FIG. 2 clearly shows how the three, representative, preventive intervals labeled there meet this safety-enhancing intention of the invention. One will note that each of these three intervals has a duration which is the most preferable duration discussed above.

Directing attention now to FIG. 3, indicated here generally at 14 is a preferred form of a system, now first of all discussed herein as being completely an anatomy-external system, constructed in accordance with the present invention for blocking, confirmedly during the ventricular relative refractory period in each of a CRM subject's cardiac cycles, the ventricular pacing activity of an associated CRM device. As was mentioned earlier herein, FIG. 3 will be described herein in manners employing it to furnish illustrations of several different structural modifications of the invention.

Included in system 14, and illustrated in block/schematic forms in this figure, are a computer-based, electronic, signal-processing structure 16, and an electronic, control-signal-generating structure, or signal generator, 18. These electronic, computer-based components, or units, within the system 14 may be constructed in any suitable and conventional fashion possessing respective architectures (software, firmware or hardware) well known to those skilled in the electronics-circuitry and computer-based arts. The computer aspect associated with these two system components, illustrated by a bracket 19, takes an appropriate form of an algorithmically programmed/programmable digital computer, and may, if desired, be distributively associated with units 16, 18. A data-informational transfer connection existing between the output side, or output, of unit 16 and the input side, or input, of unit 18 is represented by an arrow-headed line 20.

As was mentioned above in the description of FIG. 3, system 14 is shown in this figure in operative conditions relative to a conventional cardiac rhythm management (CRM) device, such as a pacemaker, 22 which, for initial illustration purposes at this point, is to be viewed as being an implanted device, and to conventional, external ECG and heart-sound sensors 24, 26, respectively. A ventricular-pacing control input conventionally provided in device 22 is operatively connected (conventionally wirelessly) to the output side, or output, of signal generator 18 via a control-signal connection represented in FIG. 3 by an arrow-headed line 28. The input side of signal-processing structure 16 is operatively connected, via arrow-headed lines 30, 32, to sensors 24, 26, respectively. Lines 30, 32 constitute input structure in structure 16. Sensor's 24, 26 are suitably and conventionally attached to the anatomy (not shown) of a CRM subject who is equipped with CRM device 22.

Device 22 is conventionally connected (not shown) within the associated CRM subject to furnish ventricular pacing pulses to the heart. A short, arrow-headed line 34, shown extending to the right in FIG. 3 from the right side of CRM device 22, represents an appropriate output terminal in device 22 for supplying (for example, wirelessly) any one of the above-mentioned other types of information—i.e., the several categories of above, representationally identified, within-ventricular-depolarization-window, measurement time marker information—to system 24 through an appropriate input terminal 35, also labeled "OTHER", in signal-processing structure 16, for user-selected employment relative to establishing blanking-interval onset. A complete connection line between output terminal 34 and input terminal 35 is not drawn in FIG. 3 in order to avoid cluttering in the figure.

Considering other system modifications and operative connections, in one, the CRM device could be an external device. In another, all, or just a part, of the components in system 14 might be integrated into such a device which could be either external or internal. In a further type of modification, relevant to the others just mentioned, sensors 24, 26 could be pluralized, and/or disposed either inside or outside of a subject's anatomy. All of these modifications are easily visualized using FIG. 3 as a basis for such visualizations.

There are, of course, other systemic modifications of the invention which may come to the minds of those skilled in the relevant art, and the present invention is intended to recognize all such other modification possibilities.

With respect to the several signal-processing and signal-handling modes of operation of system 14 herein proposed for implementation of the methodology of the invention, discussed in detail below, appropriate, conventional, algorithmic programming of the just-above-mentioned computer structure is put into place within that structure. Such programming is not specifically any part of the present invention, is designable and implementable, based upon a reading of the operational descriptions of the invention presented herein, well within the skill sets of those possessing ordinary skills in the signal-processing and computer-programming fields of art, and accordingly, is not discussed herein in detail.

Under all operating conditions, and engaging here in a general operational discussion of the system just described before turning to what is shown in FIG. 4, the system of the invention receives, cycle-by-cycle, real time, subject-specific ECG and S2 heart-sound information from sensors 24, 26. It may also be supplied with, and receive, from device 22, the above-mentioned other type(s) of within-ventricular-depolarization-window measurement time marker information.

This received information, in accordance with pre-established programming of the computer structure in system 14, is processed by structure 16, in a user-selected one of either of two different predetermined approaches (explained shortly below), so as to note, on a per-cycle basis, the times of whatever fiducial, or time-measurement markers have been selected by a user to control the duration of a pacing blanking interval, and these noted times are communicated to control-single-generating structure 18. The control-single-generating structure uses this communicated time information to establish the user-selected beginning and ending of an appropriate, related pacing blanking time interval which it applies as a CRM ventricular-pacing blanking control signal, appropriately timed, to CRM device 22.

In one of the two, above-mentioned approaches, the noted starting and ending marker times that are to be used to create preventive ventricular-pacing blanking intervals, based upon real-time information received and processed by the signal-processing structure, are determined regularly on a cycle-by-cycle basis, and because of this, may possibly differ from one another, cycle-to-cycle. In particular, preventive intervals that are employed during successive cardiac cycles in this approach are determined regularly and repetitively strictly on a cycle-after-cycle basis, whereby the data and information which has been used ultimately to establish a preventive interval that will be associated with, and employed in conjunction with, a particular, current cycle, are actually drawn from data and information directly associated with the last preceding cycle—and so on, recurrently, single-cycle after single-cycle.

In the other approach, determinations which lead to the establishments of preventive intervals are based upon data averaging drawn from predetermined-common-number, plural-cycle groups of cardiac cycles. Here, data and information received in relation to one group of such cycles are treated to produce determined averages of relevant times that relevant to that group, based upon which averages a preventive interval is generated for use in the next successive group of such cycles—and so on recurrently, cycle-group after cycle group.

Directing attention now to FIG. 4 which, in block and schematic form, illustrates the methodology of the present invention, three brackets 36, 38, 40 highlight three different ways of describing the functional nature of the present invention.

Bracket 36 highlights the methodologic, cooperative relationship between two, signal-processing blocks, 42, 44, labeled "Generating" and "Make Available", respectively. These two blocks, which are functionally linked as indicated by a directional, signal-processing flow line 46, together furnish one, high-level manner of characterizing the methodology of the invention as being a signal-processing method employable in preparation for per-cardiac-cycle prevention of the ventricular pacing operation of a cardiac-rhythm-management (CRM) subject's associated CRM device during a preventive time interval, within each of the CRM subject's cardiac cycles, which includes the ventricular relative refractory period in the cycle, this method including the steps of: (1) generating (Block 42), and then (2) making available (Block 44) for potential application to the CRM subject's associated CRM device, a ventricular-pacing blanking-time CRM control signal (Line 48) which, through appropriate method-implemented signal processing of received, real-time, CRM-subject-specific, simultaneous ECG and heart-sound, and perhaps of other information, such as measurement time marker information, has been established in relation to the timings of cardiac-cycle-specific ventricular depolarization and subsequent S2 heart-sound information.

Bracket 38, from an augmentative point of view in relation to that associated with bracket 36, highlights the methodologic, cooperative relationship between four, signal-processing blocks, including blocks 50, 52, labeled "Receiving" and "Producing", respectively, and previously mentioned blocks 42 (Generating) and 44 (Make Available). Blocks 50, 52, and 52, 42, are functionally linked, respectively, as indicated by directional, signal-processing flow lines 54, 56.

Together, these four blocks present another way of characterizing the methodology of the invention. This characterization includes (1) during a period of successive cardiac cycles, and on a per cycle basis, receiving (Block 50) the mentioned, simultaneous ECG and heart-sound and other information (via a data-reception connection represented by a line 58 extending from sensors 24, 26 and including input terminal 35), (2) employing signal processing, producing (Block 52) from such received information relevant fiducial and marker time information, (3) on a per-cycle basis, and based upon such producing, generating (Block 42) a CRM control signal which lasts throughout the appropriate blanking-time control duration, and (4) following such generating, making a so-generated CRM control signal (Line 48) available (Block 44) for application to the CRM subject's associated CRM device for appropriately preventing ventricular pacing-pulse delivery by the device during the next, successive cardiac cycle.

Bracket 40, from an even further-augmented point of view in relation to that associated with bracket 38, highlights the methodologic, cooperative relationship between seven, signal-processing blocks, including previously mentioned blocks 50 (Receiving) and 52 (Producing), new blocks 60, 62, labeled "Averaging" and "Supplying", respectively, previously mentioned blocks 42 (Generating) and 44 (Make Available), and a new block 64, labeled "Recurrently Repeating". Blocks 60, 62 are functionally linked, as indicated by a directional, signal-processing flow line 66, and are collectively sequentially, interposed blocks 52, 42, within line 56, as indicated by dashed, arrow-headed line 68 and a large dot 69. Block 64 follows block 44, within line 48, as indicated by dashed, arrow-headed line 70 and a large dot 72.

The methodologic invention associated with bracket 40 may be expressed as including the steps of (1) receiving information (Block 50) essentially as discussed above, except here in association with information drawn collectively from a selected group, or succession, of plural cardiac cycles, (2) employing signal processing, producing (Block 52) from such received, plural-cycle-group information, and generally as otherwise discussed above, relevant fiducial and marker time information, (3) averaging (Block 60) the produced time information present in a selected group of cardiac cycles, (4) supplying (Block 62) the determined average information to a signal generator, (5) generating (Block 42), by operation of the signal generator, and in relation to the determined, average information, a CRM control signal which lasts throughout the appropriate blanking-time control duration, (6) following such generating, making the generated CRM control signal (Line 48) available (Block 44) for application to the CRM subject's associated CRM device for preventing ventricular pacing-pulse delivery by the device during a next, like succession of CRM-subject cardiac cycles, and (7) recurrently repeating (Block 64) the recited receiving, calculating, averaging, supplying, generating, making-available and repeating steps.

Preferred and best-mode embodiments and manners of practicing the present invention have thus been described, along with certain variations. It will be apparent that in all modes of systemic and methodologic operation, there is substantial assurance that the likelihood for the delivery by a CRM device of an errant ventricular pacing pulse is essentially eliminated. A broad time margin is furnished with practice of the invention regarding the blocking of CRM-device pacing, and the preventive interval during which such blocking occurs definitively covers all cardiac-cycle periods of time wherein ventricular cells might, dangerously, be activatible.

Accordingly, while the invention and its key features have thus been described and illustrated herein, and certain modifications suggested, it is appreciated that other variations and modifications may be made without departing from the spirit of the invention, and it is my intention that all such other variations and modifications will be interpreted as being included within the following claims to invention.

I claim:

1. A computer-based system for blocking the ventricular pacing activity of a CRM subject's associated with CRM device so as to assure such blocking during the entirety of the ventricular relative refractory period in each of the CRM subject's cardiac cycles—with the beginning and the ending of the overall period of such blocking in each cardiac cycle being system-defined to lie, respectively, (a) within the real-time, ventricular depolarization window in the cycle, and (b) at the time of the real-time, S2 heart-sound, plus or minus any user-defined time-delta, said system comprising a signal-processing structure having information input structure adapted to receive, for processing, real-time, cardiac-cycle-specific ECG and heart-sound information derived from such a CRM subject, and an output for supplying processed ECG and heart-sound information, and control-signal-generating structure disposed downstream from said signal-processing structure, including an input operatively connected to said output for receiving processed information therefrom, and for generating, in relation to such received, processed information, a CRM pacing control signal designed to effect CRM-device pacing-activity blocking during the mentioned overall period of such blocking.

2. The system of claim 1, which is at least partially integrated with the CRM subject's associated CRM device.

3. The system of claim 1 which is constructed whereby the beginning of blocking associated with the mentioned overall period of blocking occurs at the onset of ventricular depolarization.

4. The system of claim 1 which is constructed whereby the beginning of blocking associated with the mentioned overall period of blocking occurs adjacent the peak of the R-wave.

5. The system of claim 1 which is constructed whereby the beginning of blocking associated with the mentioned overall period of blocking occurs at the time of the S1 heart sound.

6. The system of claim 1 which is constructed whereby the beginning of blocking associated with the mentioned overall period of blocking occurs adjacent the conclusion of the ventricular depolarization window.

7. The system of claim 1, wherein said signal-processing and control-signal-generating structures are constructed to establish plural-cycle-group pacing blocking based upon averaged information drawn from, and signal processed by these two system structures in relation to, system-received cardiac-cycle information associated with plural, CRM-subject-specific cardiac cycles that are present in selected, successive, plural-cycle groups of CRM-subject-specific cardiac cycles.

8. A signal-processing method employable in preparation for per-cardiac-cycle blanking of the ventricular pacing operation of a CRM subject's associated CRM device during a blanking time interval within each of the CRM subject's cardiac cycles, which interval always includes the entirety of the ventricular relative refractory period in the cycle, said method including the steps of generating, and then making available for potential application to the CRM subject's associated CRM device, a ventricular-pacing blanking-time CRM control signal which, through appropriate method-implemented signal processing of received, real-time, CRM-subject-specific, simultaneous ECG and heart-sound information, has been established with a duration possessing a beginning and an ending defined to lie, respectively, (a) within the real-time, ventricular depolarization window in the cycle, and (b) at the time of the real-time, S2 heart-sound, plus or minus any user-defined time-delta.

9. The method of claim 8 wherein said generating is performed whereby the beginning of ventricular-pacing blanking occurs at the onset of ventricular depolarization.

10. The method of clam 8 wherein said generating is performed whereby the beginning of ventricular-pacing blanking occurs adjacent the peak of the R-wave.

11. The method of claim 8 wherein said generating is performed whereby the beginning of ventricular-pacing blanking occurs at the time of the S1 heart sound.

12. The method of claim 8 wherein said generating is performed whereby the beginning of ventricular-pacing blanking occurs adjacent the conclusion of the ventricular depolarization window.

13. The method of claim 8 which involves plural-cycle-group pacing blanking based upon averaged information drawn from, and signal processed in relation to, cardiac-cycle information associated with plural, CRM-subject-specific cardiac cycles that are present in selected, successive, plural-cycle groups of CRM-subject-specific cardiac cycles.

14. A signal-processing method useable in relation (a) to a cardiac-rhythm-management (CRM) subject equipped with a CRM device, and (b) to the availability of real-time, simultaneous, CRM-subject-specific, ECG and heart-sound information, implementable during a period embracing a plurality of successive, CRM-subject cardiac cycles for assuring, during each of those cycles, that no CRM-device-initiated, ventricular pacing pulse may be delivered to the CRM subject within a blanking-time control duration in the cycle which extends from adjacent the onset of the electromechanical systole in the cycle to adjacent a point in time disposed effectively at the end of the cycle's ventricular relative refractory period, said method comprising during the mentioned period of successive cycles, and on a per-cycle basis, receiving the mentioned, simultaneous ECG and heart-sound information,
employing signal processing, producing, from such per-cycle received information, selected, associated, noted information, including (a) the associated time span of the electromechanical (EM) systole, and (b) the associated times of selected, ECG and heart-sound fiducial markers, lying within the ventricular depolarization window in the EM systole,
on a per-cycle basis, and based upon said producing, generating a CRM control signal which lasts throughout the mentioned blanking-time control duration, and
following said generating, making a so-generated CRM control signal available for application to the CRM subject's associated CRM device for preventing ventricular pacing-pulse delivery by the device during the next, successive cardiac cycle.

15. A signal-processing method useable in relation (a) to a cardiac-rhythm-management (CRM) subject equipped with a CRM device, and (b) to the availability of real-time, simultaneous, CRM-subject-specific, ECG and heart-sound information, implementable during a period embracing a plurality of successive, CRM-subject cardiac cycles for assuring, during each of those cycles, that not CRM-device-initiated, ventricular pacing pulse may be delivered to the CRM subject within a blanking-time control duration in the cycle which extends from adjacent the onset of the electromechanical systole in the cycle to adjacent a point in time disposed effectively at the end of the cycle's ventricular relative refractory period, said method comprising during the mentioned period of successive cycles, and on a per-cycle basis, receiving the mentioned, simultaneous ECG and heart-sound information,
employing signal processing, producing, from such per-cycle received information, selected, associated, noted information, including (a) the associated time span of the electromechanical (EM) systole, and (b) the associated times of selected, ECG and heart-sound fiducial markers, lying within the ventricular depolarization window in the EM systole,
averaging the time information associated with the noted information relating to a selected group of cardiac cycles, and thereby establishing available, noted, average information for the selected group,
supplying the established, available, noted average information to a signal generator,
generating, by operation of the signal generator, and in relation to the established, available, noted average information, a CRM control signal which lasts throughout the mentioned blanking-time control duration,
following said generating, making the generated CRM control signal available for application to the CRM subject's associated CRM device for preventing ventricular pacing-pulse delivery by the device during a next, like succession of CRM-subject cardiac cycles, and
recurrently repeating the recited receiving, producing, averaging, supplying, generating, marking-available and repeating steps.

* * * * *

UNITED STATES PATENT AND TRADEMARK OFFICE
CERTIFICATE OF CORRECTION

PATENT NO. : 8,548,588 B1
APPLICATION NO. : 13/624679
DATED : October 1, 2013
INVENTOR(S) : Peter T. Bauer Page 1 of 1

It is certified that error appears in the above-identified patent and that said Letters Patent is hereby corrected as shown below:

In the Specification

Column 12, line 20, please replace "not" with --no--.
Column 12, line 53, please replace "marking-available" with --making-available--.

Signed and Sealed this
Twelfth Day of November, 2013

Teresa Stanek Rea
*Deputy Director of the United States Patent and Trademark Office*